(12) United States Patent
Nix et al.

(10) Patent No.: US 6,238,347 B1
(45) Date of Patent: May 29, 2001

(54) ULTRASONIC TRANSDUCER ARRAY AND METHOD OF MANUFACTURING THE SAME

(75) Inventors: Elvin Leonard Nix, London (GB); George Woodrow Keilman, Woodinville, WA (US); Robert Julian Dickinson, London (GB)

(73) Assignee: Intravascular Research Limited, London (GB)

(*) Notice: Subject to any disclaimer, the term of this patent is extended or adjusted under 35 U.S.C. 154(b) by 0 days.

(21) Appl. No.: 08/940,919

(22) Filed: Sep. 30, 1997

Related U.S. Application Data

(62) Division of application No. 08/402,143, filed on Mar. 10, 1995, now abandoned.

(30) Foreign Application Priority Data

| Mar. 11, 1994 | (GB) | .................................................. 9404782 |
| Sep. 9, 1994 | (GB) | .................................................. 9418156 |

(51) Int. Cl.⁷ ............................................................ A61B 8/12
(52) U.S. Cl. ............................................. 600/463; 600/467
(58) Field of Search .................................... 600/459, 462, 600/463, 466, 467, 447, 468, 472

(56) References Cited

U.S. PATENT DOCUMENTS

| 4,440,025 | * | 4/1984 | Hayakawa et al. ...................... 73/642 |
| 4,841,977 | | 6/1989 | Griffith et al. . |
| 4,869,768 | | 9/1989 | Zola . |
| 4,917,097 | | 4/1990 | Proudian et al. . |
| 5,042,493 | * | 8/1991 | Saito et al. ............................. 600/459 |
| 5,044,053 | | 9/1991 | Kopel et al. . |
| 5,081,993 | | 1/1992 | Kitney et al. . |
| 5,135,001 | * | 8/1992 | Sinofsky et al. ...................... 600/462 |
| 5,186,177 | | 2/1993 | O'Donnell et al. . |
| 5,240,004 | | 8/1993 | Walinsky et al. . |
| 5,257,629 | | 11/1993 | Kitney et al. . |
| 5,275,167 | | 1/1994 | Killam . |
| 5,368,037 | | 11/1994 | Eberle et al. . |
| 5,456,259 | | 10/1995 | Barlow et al. . |
| 5,740,808 | * | 4/1998 | Panescu et al. ....................... 600/459 |

FOREIGN PATENT DOCUMENTS

| 0145429 | 6/1985 | (EP) . |
| 2258364 | 2/1993 | (GB) . |
| WO 8809150 | 12/1988 | (WO) . |
| WO 9417734 | 8/1994 | (WO) . |

OTHER PUBLICATIONS

Declaration of Robert J. Dickinson, and Attachments A–C.
Complaint by Endosonics against IRL, and Attachments A–H.
Complaint by IRL against Endosonics, and Attachments A–B.

* cited by examiner

Primary Examiner—Francis J. Jaworski
(74) Attorney, Agent, or Firm—Richard M. Goldberg

(57) ABSTRACT

In a method of manufacturing an ultrasonic transducer array a plurality of discrete transducer elements are formed on an initially flat flexible substrate together with electrically conductive tracks, through which the transducer elements will be energised in use, the flexible substrate with the discrete transducer elements and conductive tracks mounted thereon then being formed into a cylinder and mounted on the end of a catheter tube, the substrate being radially outwardly of the transducer elements so that it is in a position to act also as an acoustic matching layer between the material of the transducer elements and the human tissues or blood when in use.

6 Claims, 14 Drawing Sheets

ULTRASONIC TRANSDUCER ARRAY AND METHOD OF MANUFACTURING THE SAME

This application is a division, of application Ser. No. 08/402,143 filled Mar. 10, 1995 now abandoned.

FIELD OF THE INVENTION

The present invention relates to an ultrasonic transducer array and a method of manufacturing the same.

BACKGROUND OF THE INVENTION

In our co-pending application number 9116478 there is disclosed an ultrasonic transducer array for use in visualising the internal organs of the human body, for example in a system as disclosed in our UK Patents 2,212,267 and 2,233,094. As explained in our earlier co-pending application number 9116478 there are considerable problems to overcome in manufacturing such a transducer array because of its extremely small size.

A method of manufacture disclosed in our above mentioned co-pending application number 9116478 gives a high performance ultrasonic transducer but it is relatively expensive to manufacture. There are other advantages to this method of manufacture, relating to i) the ability to have well-designed acoustic layers, ii) the removal of the need to have a rigid (tungsten carbide) support and iii) the concomitant increase in backing layer thickness.

SUMMARY OF THE INVENTION

According to a first aspect of the present invention in a method of manufacturing an ultrasonic transducer array a plurality of discrete ceramic transducer elements are formed on an initially flat flexible substrate together with electrically conductive tracks, through which the transducer elements will be energised in use, the flexible substrate with the discrete transducer elements and conductive tracks mounted thereon then being formed into a cylinder, the substrate being radially outwardly of the transducer elements, According to a second aspect of the present invention the substrate comprises at least two laminae, a first lamina being flexible and acting as the second part of a two layer matching layer and having the conductive tracks thereon and a second lamina being sandwiched between said first lamina and said transducer elements which are carried thereon, the second lamina having a higher acoustic impedance than the first lamina and acting as the first part of the two layer matching layer.

According to a third aspect of the present invention the first lamina is in the form of a film which is deposited on the flexible substrate.

According to a fourth aspect of the present invention the flat assembly comprising the substrate, the transducer array and the conductive tracks is shaped into a cylinder by means of a mould. The mould may comprise two semi-circular cross-section mould elements to which suction may be applied to draw the flat assembly into the mould in order to make it confirm to the shape of the inside of the mould elements.

According to a fifth aspect of the present invention the flat assembly comprising the substrate, the transducer array and the conductive tracks is then drawn through a guide member constructed so that the flat assembly is progressively shaped into a cylinder.

According to a sixth aspect of the present invention a multiplexing circuit is provided on the flexible substrate.

According to a seventh aspect of the invention the multiplexing circuit includes an integrated circuit which is flip-chip bonded in position.

According to an eighth aspect of the present invention the multiplexing circuit is made up of a plurality of individual integrated circuits arranged in a polygonal configuration.

According to ninth aspect of the present invention the polygon comprises a square.

According to a tenth aspect of the present invention there is an annular space between the assembled circular transducer array and the distal end of the catheter, this gap being filled with a material which acts both as an adhesive and as an acoustic backing layer.

According to an eleventh aspect of the present invention an earth return on the top of the piezo-electric transducer is electrically connected to an earth return on the bottom of the substrate to thereby form a common return.

BRIEF DESCRIPTION OF THE DRAWINGS

How the invention may be carried out will now be described by way of example only and with reference to the accompanying drawings in which.

DETAILED DESCRIPTION OF THE DRAWINGS

FIG. 1

Figure 1:
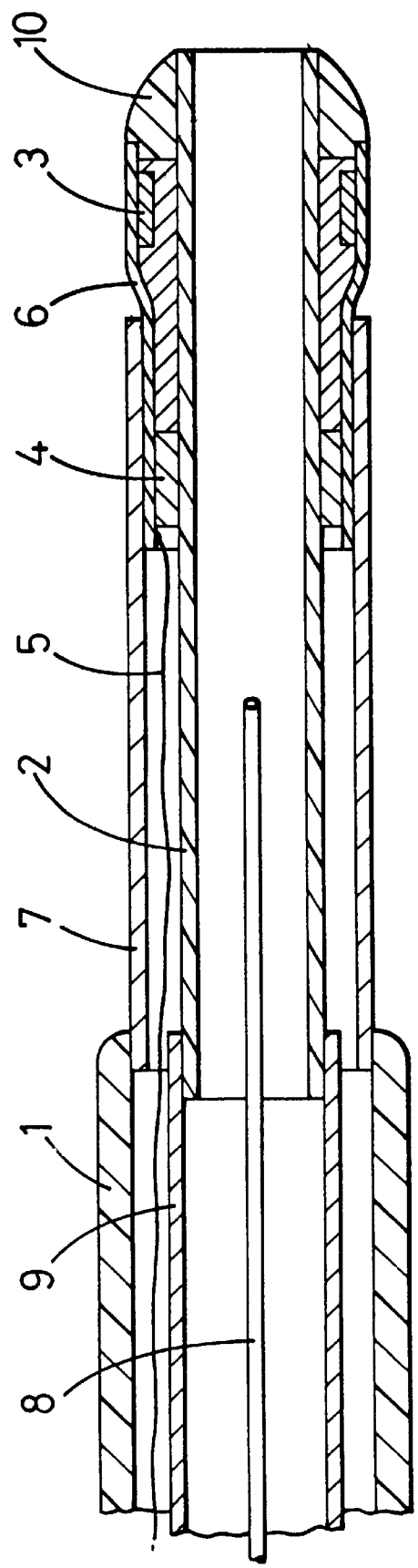
FIG. 1 is a longitudinal sectional view of the distal end of a catheter carrying a transducer array of the kind to which the present invention may be applied.

FIG. 1 illustrates a known type of catheter comprising a, main flexible plastic tubular body 1 to the distal end of which is mounted a flexible plastic tubular body member 2, the latter being typically about twenty five centimetres long. The distal end of the body 2 carries an ultrasonic transducer array 3 which is made up, in this embodiment, of sixty four discrete transducer elements made of a ceramic material such as PZT. Associated with and electrically connected to this array is a multiplexer arrangement 4 which is in turn electrically connected to apparatus (not shown) at the proximal end of the catheter by electrically conducting leads 5. That apparatus may comprise the system disclosed in our UK Patents 2,212,267 and 2,233,094.

The transducer array 3 and multiplexer arrangement 4 are carried by a flexible substrate 6 and (see FIGS. 2 and 3) it is this sub-assembly with which the present invention is concerned.

The tip body 2 has a sleeve 7 which is secured at its proximal end to the distal end of the main catheter body 1 and at its distal end to the substrate 6.

The tip body 2 is connected to a main inner body 9, and the catheter has the usual known guide wire 8 associated with it.

The distal end of the assembly as a whole is provided with a so-called "soft-tip" in the form of a moulding 10 which is shaped to facilitate the insertion and positioning of the catheter into the artery of a patient.

The multiplexer 4 and transducer array 3 are energised and echo signals transmitted through electrical leads 5.

The purpose of FIG. 1 is to illustrate an example of one type of catheter construction to which the present invention may be applied, this construction being known as an "over-the-wire" design. However, the present invention has general application to other types of catheter construction, including that known as the "rapid exchange" or "monorail" design, and is not limited to this particular application, the present invention being concerned with the construction and method of manufacturing the transducer array 3 and multiplexer 4 assembly and not the general construction of the catheter as such.

Figure 2:
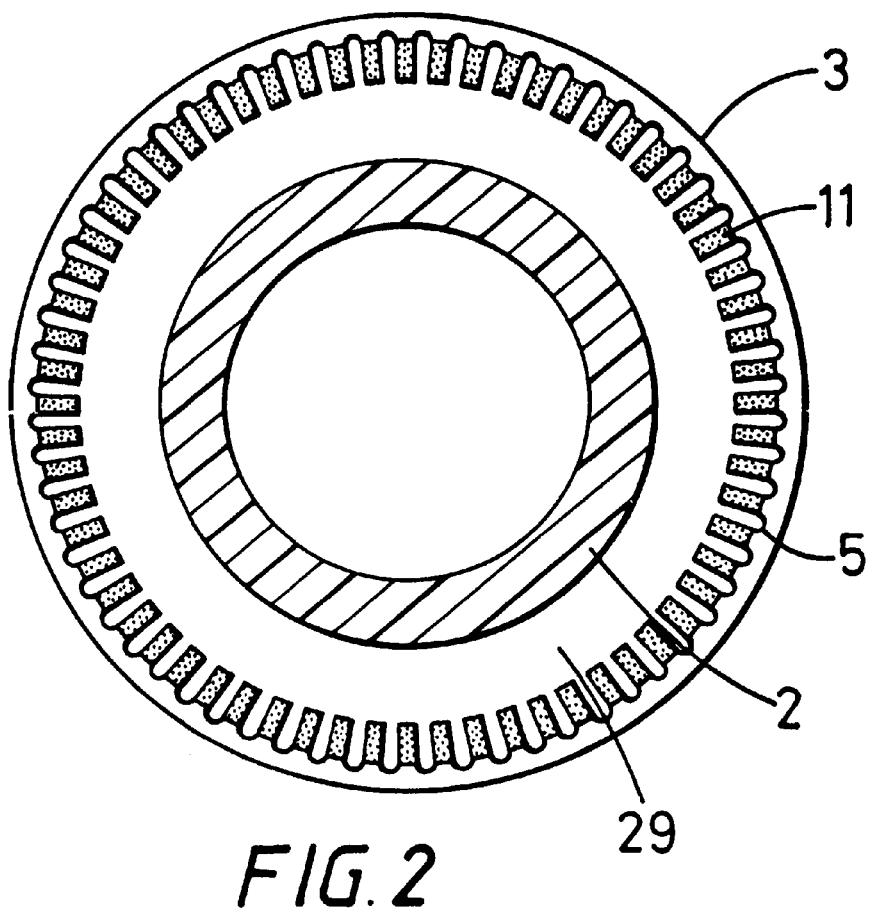
FIG. 2 is a cross-sectional view of a first embodiment of the present invention.
Figure 3:
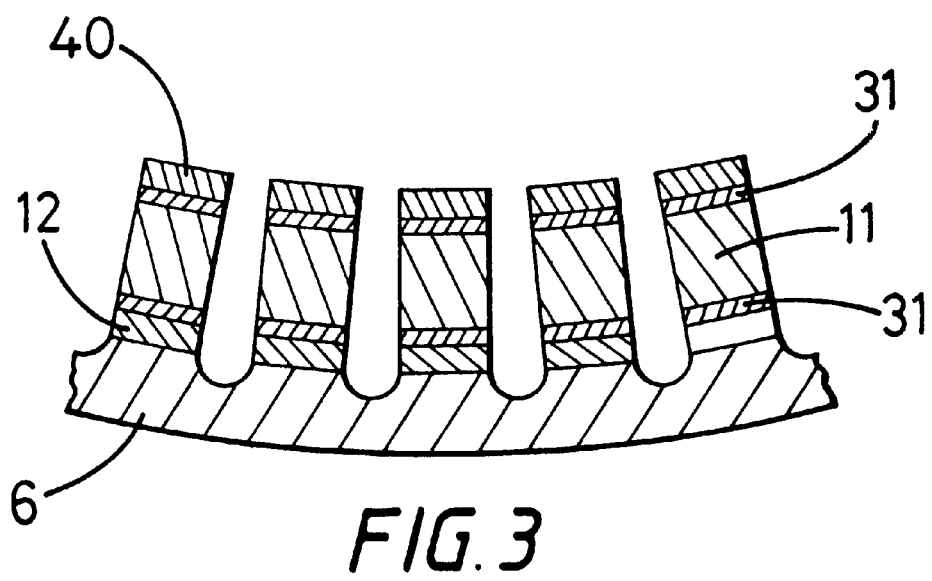
FIG. 3 is an enlarged cross-sectional fragmentary view of an alternative to FIG. 2.

The invention will now be described with reference to the remaining figures of the drawings.
FIGS. 2 and 3

FIG. 2 shows a transducer array 3 which comprises sixty four discrete piezo-electric ceramic transducer elements 11, made of PZT, has a circular cylindrical configuration and is carried by a cylindrical flexible substrate 6 of polyimide which is located radially outwardly with respect to the transducer array 3.

The flexible substrate 6 can thus also act as an acoustic matching layer between the piezo-electric ceramic transducer elements and human tissues or blood of the patient. More specifically the flexible substrate 6 can be made of the polyimide material known as "Upilex-S", the acoustic impedance of which is close to the optimum required for acoustic matching between the piezo-electric ceramic material of the transducer elements and human tissues or blood. This acoustic impedance is approximately 3.5 MRayls.

FIG. 3 shows a variation on the construction shown in FIG. 2. In THISvariation there is a further layer 12 of material between the flexible polyimide substrate 6 and the piezo-electric transducer elements 11.

The layer 12 comprises a material which is electrically conductive and has a higher acoustic impedance of around 10 MRayls. The layer 12 may comprise magnesium, a conductive epoxy resin or a conductive glass.

In this embodiment the flexible substrate 6 may be made of a lower acoustic impedance material than that of the embodiment of FIG. 2. For example, in the embodiment of FIG. 3 the flexible substrate may comprise a polyimide material such as "Kapton" (registered trade mark) having an acoustic impedance of around 2.5 MRayls. The advantage of this embodiment is that the polyimide substrate 6 can in fact be formed as a flat film and this can be carried out very accurately, typically to a tolerance of a few microns.

There are two metallised layers 31 in the positions indicated in FIG. 3. These would apply to both the embodiments of FIGS. 2 and 3. In addition there is a copper coated polyimide film 40 secured by adhesive to the top of the piezo-electric material 11 which will be described in more detail in relation to FIGS. 9 and 10.
FIGS. 4 to 10

Figure 4:
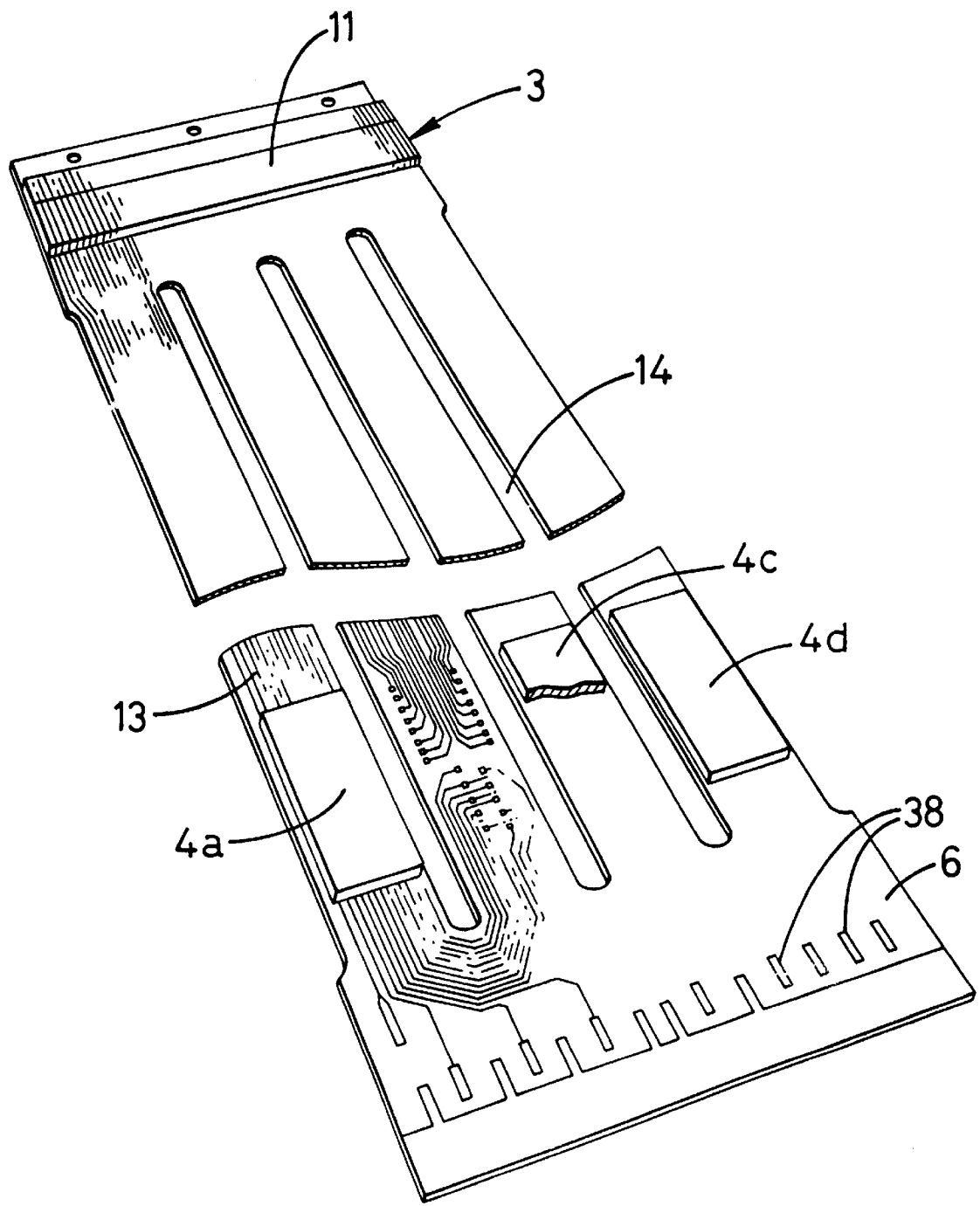
FIG. 4 is a perspective three quarter view showing a transducer array and associated multiplexer units in-the-flat condition.
Figure 5:
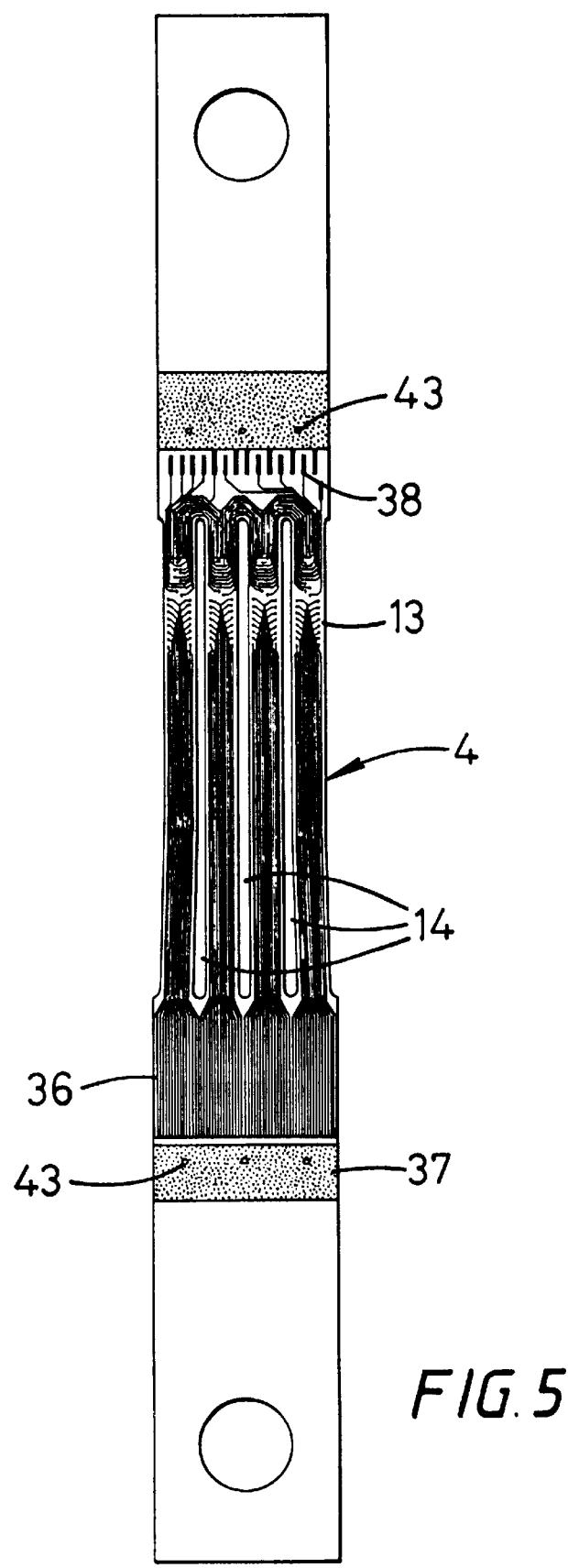
FIG. 5 is a plan view showing the detailed circuitry of the arrangement shown in FIG. 4.
Figure 6:
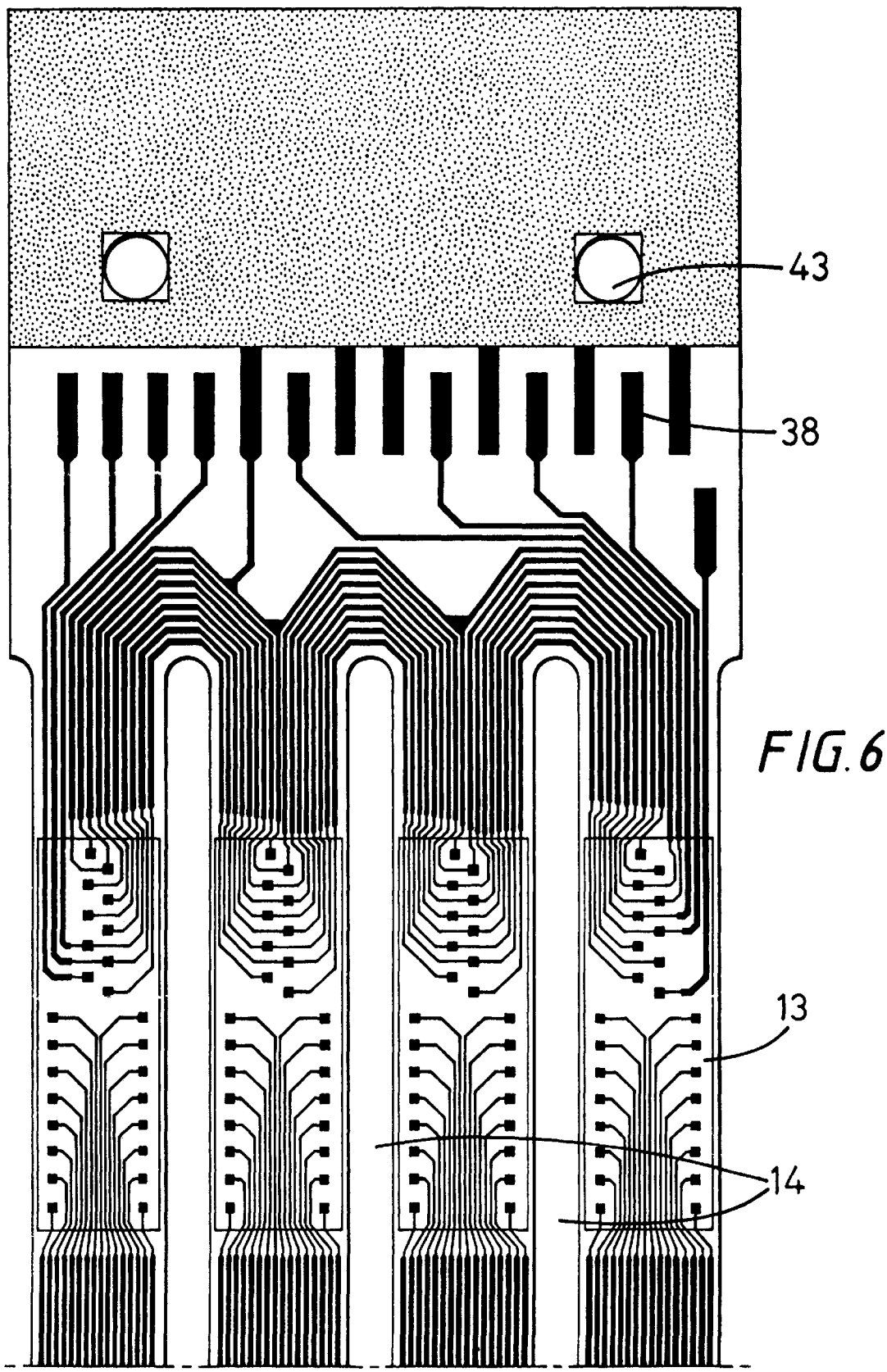
FIG. 6 is an enlarged fragmentary view of part of FIG. 5.
Figure 7:
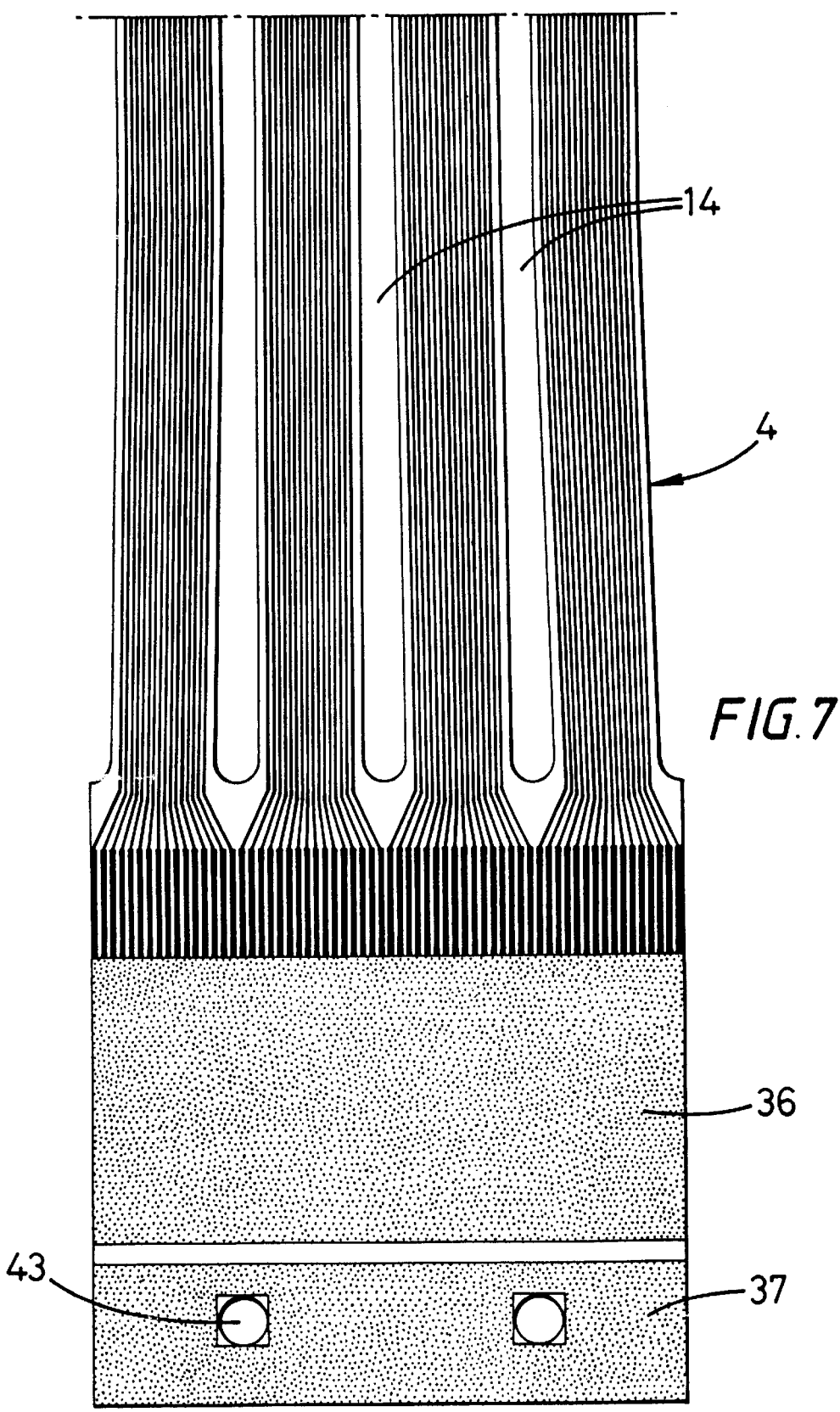
FIG. 7 is an enlarged fragmentary view of another part of FIG. 5.

The transducer array 3 and multiplexer 4 arrangement is first manufactured in-the-flat as shown in FIGS. 4 and 5. It is then wrapped or rolled into the configuration shown in FIG. 8.

As indicated earlier the transducer array 3 comprises sixty four transducer elements 11 which are electrically connected to four 16-channel multiplexer chips 4a, 4b, 4c and 4d (4b being omitted for clarity and 4c being only partially shown).

The advantage of initially manufacturing the assembly shown in FIG. 4 in-the-flat is that it is easier to manufacture because firstly forming the various components in-the-flat rather than on a cylindrical surface is inherently easier and secondly it is possible to use standard production equipment. More particularly standard printed circuit and integrated circuit production methods can be employed. A further advantage, is that the thickness of flat material is easier to control to high accuracy than the wall thickness of cylindrical components.

The transducer array 3 consists of functionally discrete ceramic elements mounted on the flexible substrate 6.

As indicated earlier, each multiplexer is in the form of an integrated circuit and this integrated circuit can itself be flip-chip bonded to the circuit comprising electrical connections 13 which are formed on the substrate 6 by means of known printed circuit techniques.

The transducer array 3 which consists of functionally discrete ceramic elements, is manufactured using the following steps.

The polyimide substrate material 6 is plated on both sides, with a 1–2 micron thickness of copper at 39 and 40, typically by a two stage process in which vacuum deposition or sputtering is used to give a thin base coat of good allocation, and chemical plating techniques to increase the copper thickness to the desired value.

The conductive tracks 13 are then formed in the layer 39 on one side of the substrate by a standard photolithography technique followed by chemical etching or ion-beam milling to form the circuit pattern as shown in FIG. 5.

A block of piezo-electric material 11 having the desired radial thickness of the final transducer elements and coated on both sides by a metallisation layer 31, is bonded in one piece to an area of the copper layer 39 which is shaped to define a connection pad 36 on the substrate. The bonding is effected by a suitable adhesive 35 which could comprise a low viscosity epoxy resin.

The polyimide substrate 6 has a copper layer 40 on its bottom surface.

The piezo-electric transducer array, in use, would be energised through the copper layer 39, the upper metallised layer 31 on the top of the piezo-electric ceramic transducer block 11 forming an earth return path and being electrically connected to the copper layer 40 to thus form a common return path.

Figure 9:
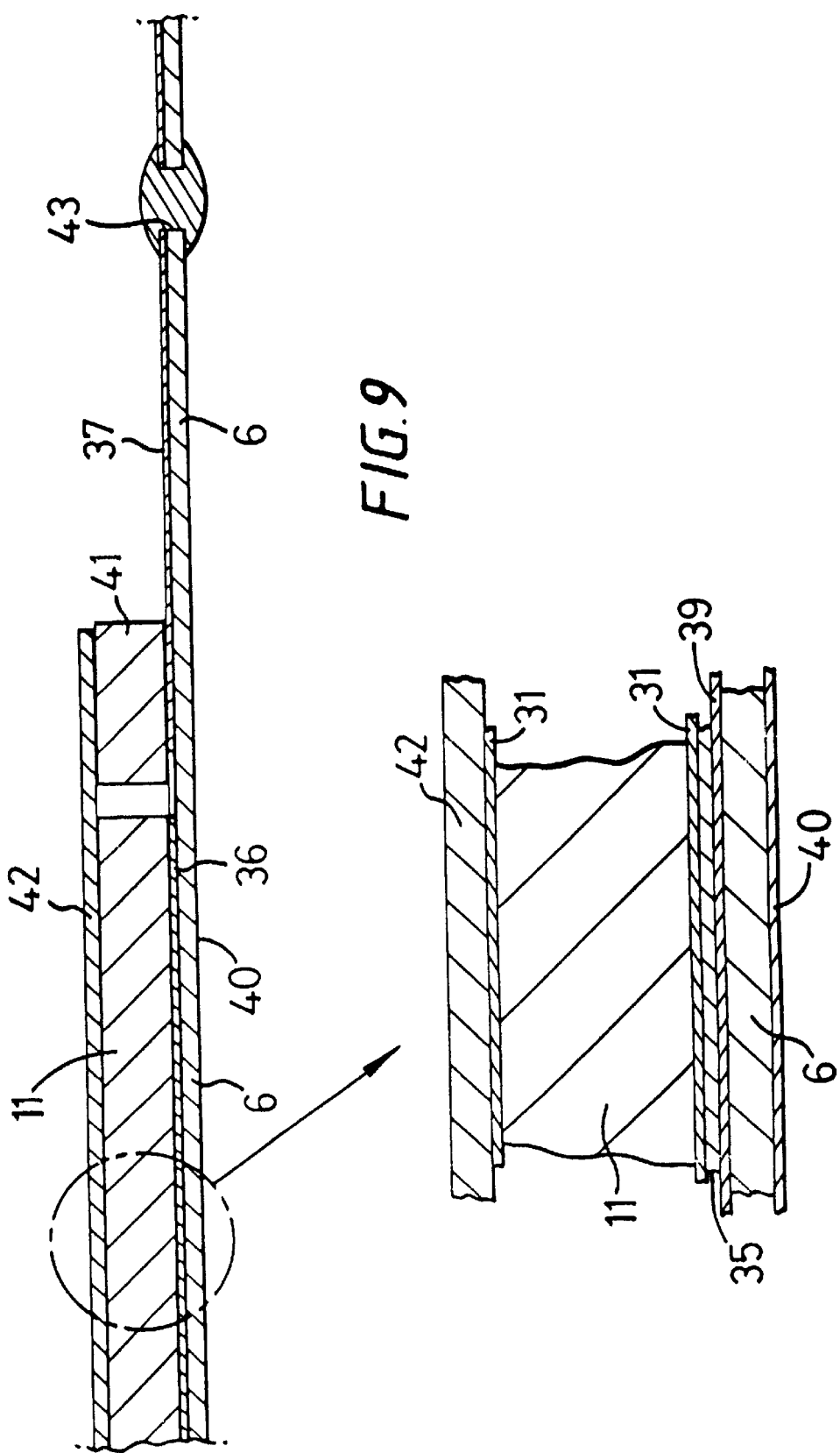
FIG. 9 is a half-elevational cross-section showing a first arrangement for providing a common return electrical path for the transducer array.
Figure 10:
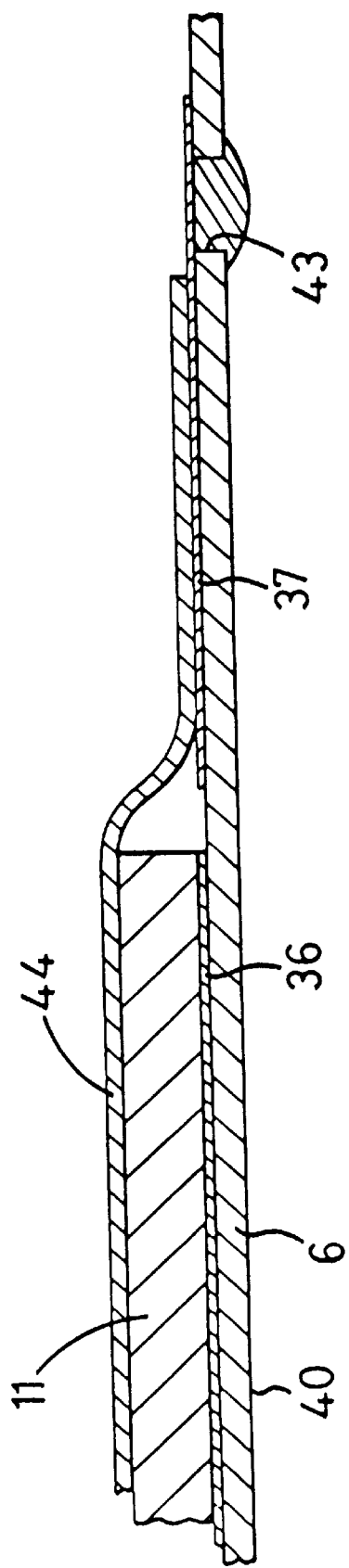
FIG. 10 is similar to FIG. 9 but showing a second arrangement for providing a common return electrical path for the transducer array.

This can be achieved in a number of ways, two of which are shown in FIGS. 9 and 10 respectively.

In FIG. 9 the return path is provided by a graphite block or rectangle 41 mounted on a second connection pad 37. A piece of copper coated polyimide film 42 connects the top of the piezo ceramic element 11 to the graphite 41. The second connection pad 37 is electrically connected to the lower ground copper layer 40 by means of electrically conducting material through via holes 43.

In the alternative construction shown in FIG. 10 the graphite block 41 is replaced by a flexible copper film 44 which is bonded to the top of the PZT block 11 and to the second connection pad 37.

The construction shown in FIG. 9 is preferred as it is easier to assemble and also easier to form cuts in the graphite block than in the flexible film 44.

The bonding of the various interfaces has to have adequate mechanical strength, maintain electrical contact, and is performed preferably using a suitable low-viscosity adhesive, such as with a controlled force press, so that the adhesive thickness is less than the roughness of the two surfaces, a standard method used in sensor construction.

The ceramic block 11 is then diced into separate transducer elements 11a, 11b . . . 11n using a diamond saw. Each saw cut 45 is arranged to penetrate into the substrate 6 by up to one half its thickness (as shown in FIG. 3), which will separate the connection pad 36 into separate tracks, which are arranged to align and be contiguous with the circuit tracks previous defined.

In order to keep the return on the second connection pad 37 common, the length of the saw cuts is arranged to traverse the second connection pad 37. This can be done by a technique known as "plunge-cutting" in which the sawblade height is varied as the blade makes its cut. Thus, the part of the second connection pad 37 supporting the graphite block 41 or the copper film 44 connection is diced, but the rest is not.

Slots 14 are formed between adjacent multiplexer chips 4a,4b; 4b,4c; and 4c,4d.

The purpose of the slots 14 is to render the substrate 6 easily bendable along the lines of the slots and to remove material so that there can be a relatively gradual transition from the cylindrical configuration of the transducer array 3 to the rectangular configuration of the four multiplexer chips 4 (a)(b)(c) and (d) shown in FIG. 4 thus minimising the building in of stress. In addition the relatively long distance between the transducer array 3 and the multiplexers 4 enables the final assembly to bend as it passes along a patient's artery (see FIG. 8) which would not be the case if elements 3 and 4 were close together.

The multiplexer chips thus form a four sided polygon which in this embodiment is a square. FIG. 5 shows the arrangement of FIG. 4 in more detail and accuracy, the same reference numerals being used to indicate equivalent elements.

The most convenient mechanical implementation of the multiplexed array is to have four identical integrated circuits each connected to a quarter of the transducer array. When wrapped so that the transducer elements form a cylinder, the area where the multiplexers are mounted will tend to form a square section and in order to relieve mechanical stresses in the flexible substrate on the corners of the square section and in the transition region between the circular and square sections it is advantageous to put the slots 14 in the flexible substrate 6 as referred to earlier. Because a square has a greater maximum dimension than a circle of the same perimeter it is preferable that the slots have a significant width in order to remove material from the corner of the square parameter so that the cross-section at the level of the multiplexers fits inside the final diameter of the circular transducer array.

FIG. 5 shows the pattern of the flexible circuit with such slots.

The slots 14 can be formed by a variety of processes such as laser cutting, chemical etching, mechanical punching or mechanical milling.

FIG. 5 shows that the multiplexer integrated circuits 4 are mounted some distance from the transducer array 3 which thus allows the section around the multiplexers to be slightly larger if necessary than the array without significantly affecting the ability of the catheter to access and image narrow vessels. This distance also gives the advantage referred to earlier in that the transducer array/multiplexer assembly can negotiate bends and curves in the patient's artery without undue resistance.

The integrated circuits are fabricated with bumps of tin-lead solder attached to their connector pads. They are then aligned over the electrical connection 13 using a flip-chip alignment system, and placed on the substrate. The circuit is then heated to allow solder reflow to occur, which permits a degree of self-alignment of the integrated circuit due to the surface tension of the molten solder. It is this self-alignment that makes the solder reflow system a suitable process, and preferable over indium/gold thermal diffusion or gold/gold thermosonic processes. It also permits the use of copper on the substrate, with its cost advantages.

FIGS. 11 to 15

Figure 14:
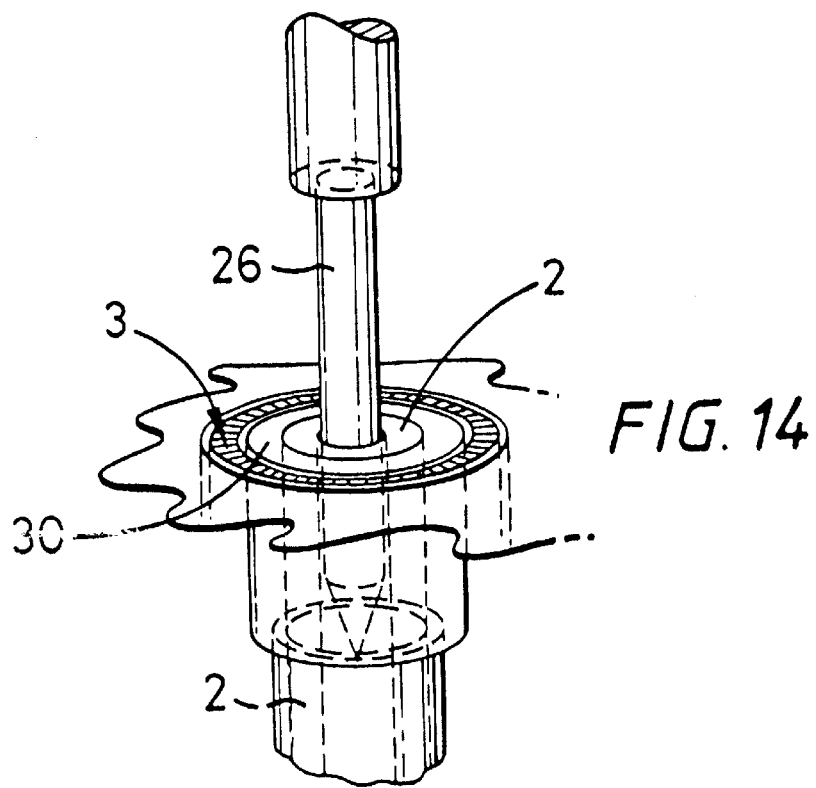
FIG. 14 is an even more enlarged fragmentary view showing part of the apparatus shown in FIG. 9.
Figure 13:
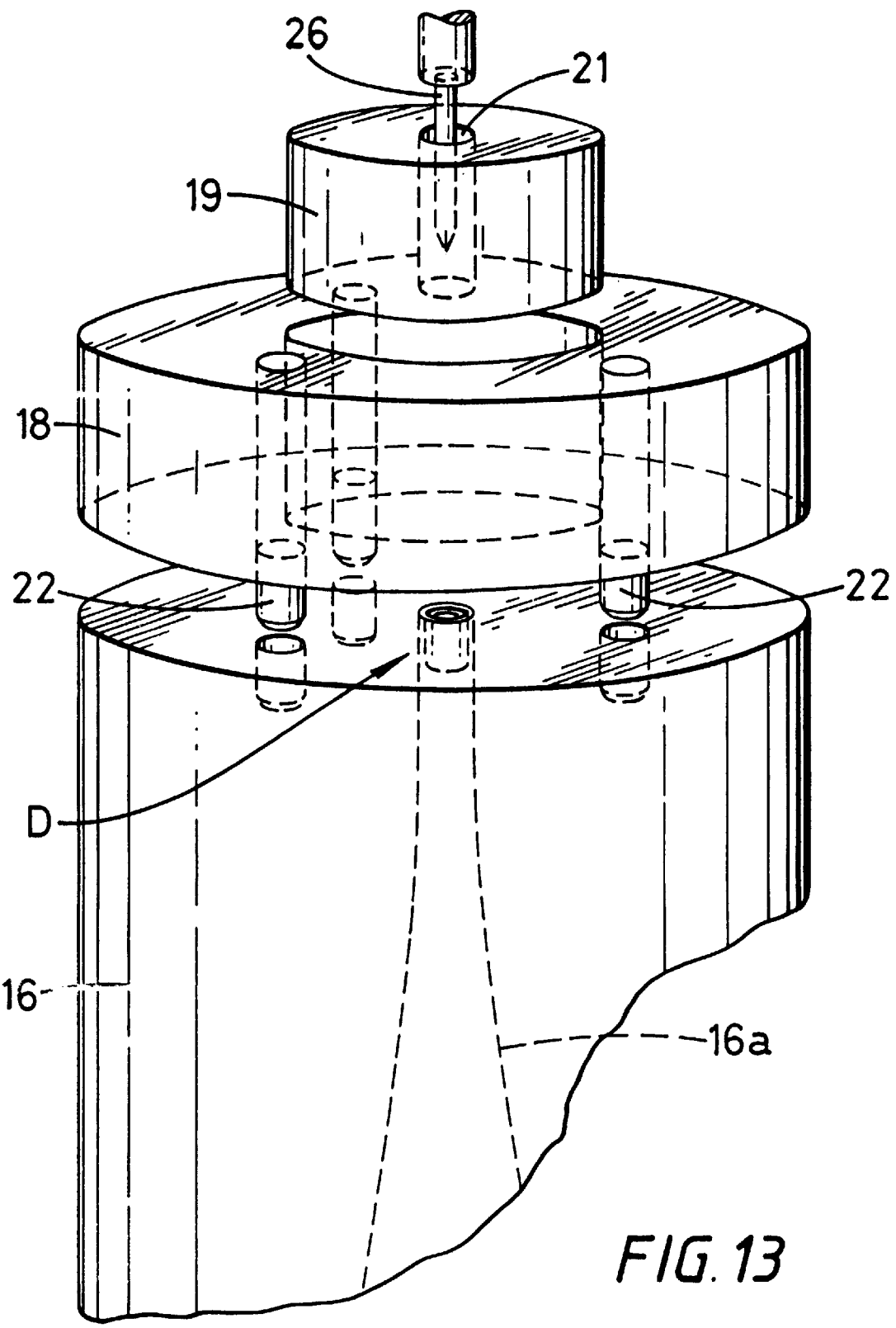
FIG. 13 is an enlarged exploded view of the part of the apparatus shown in FIG. 9.

FIGS. 13 and 14 illustrate diagrammatically one form of apparatus which can be used to manufacture the combined transducer array and multiplexer arrangement shown in FIGS. 4 to 10.

The way in which this apparatus is used to transform the flat arrangement shown in FIGS. 4 to 7 into the cylindrical/square arrangement shown in FIG. 8, and to secure that latter arrangement in position at the distal end of the catheter 1 will now be described.

The basic steps involved in using the apparatus shown in FIGS. 11 to 14 both to form and to secure the transducer/multiplexer assembly to the distal end of the catheter are as follows.

First a mould assembly 15 (FIG. 11) is used to make a funnel shaped die member 16 (FIGS. 12 and 13) which can either be used several times to produce several complete catheters or can be used only once to produce a single catheter, a further mould die 16 then being formed to enable the next catheter to be produced.

Figure 8:
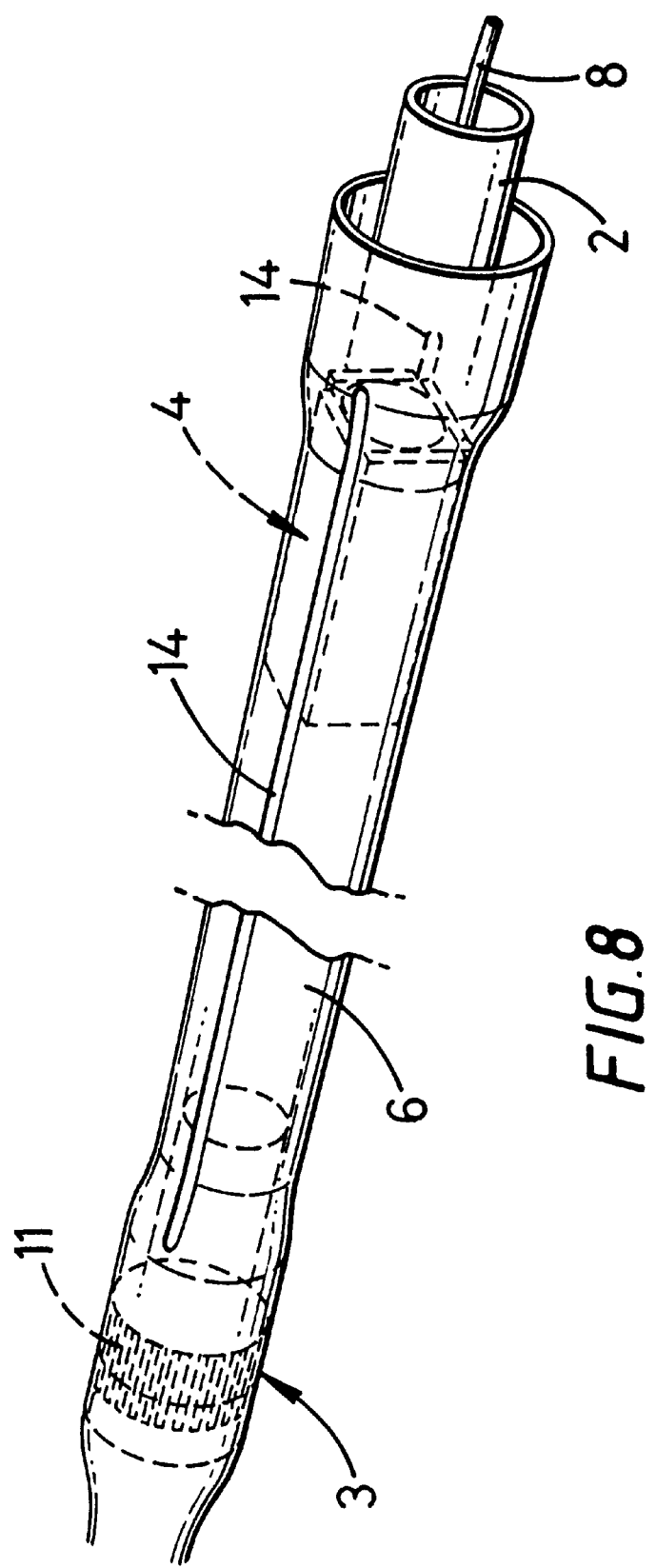
FIG. 8 shows the arrangement of FIG. 4 assembled into its final cylindrical condition.

The die 16 is then used to convert the flat transducer/multiplexer arrangement of FIGS. 4 to 7 into the cylindrical configuration shown in FIG. 8.

Finally the cylindrical transducer/multiplexer arrangement of FIG. 8 is fixedly mounted on the distal end of the catheter.

These steps will now be described in more detail with reference to FIGS. 11 to 14.

Figure 11:
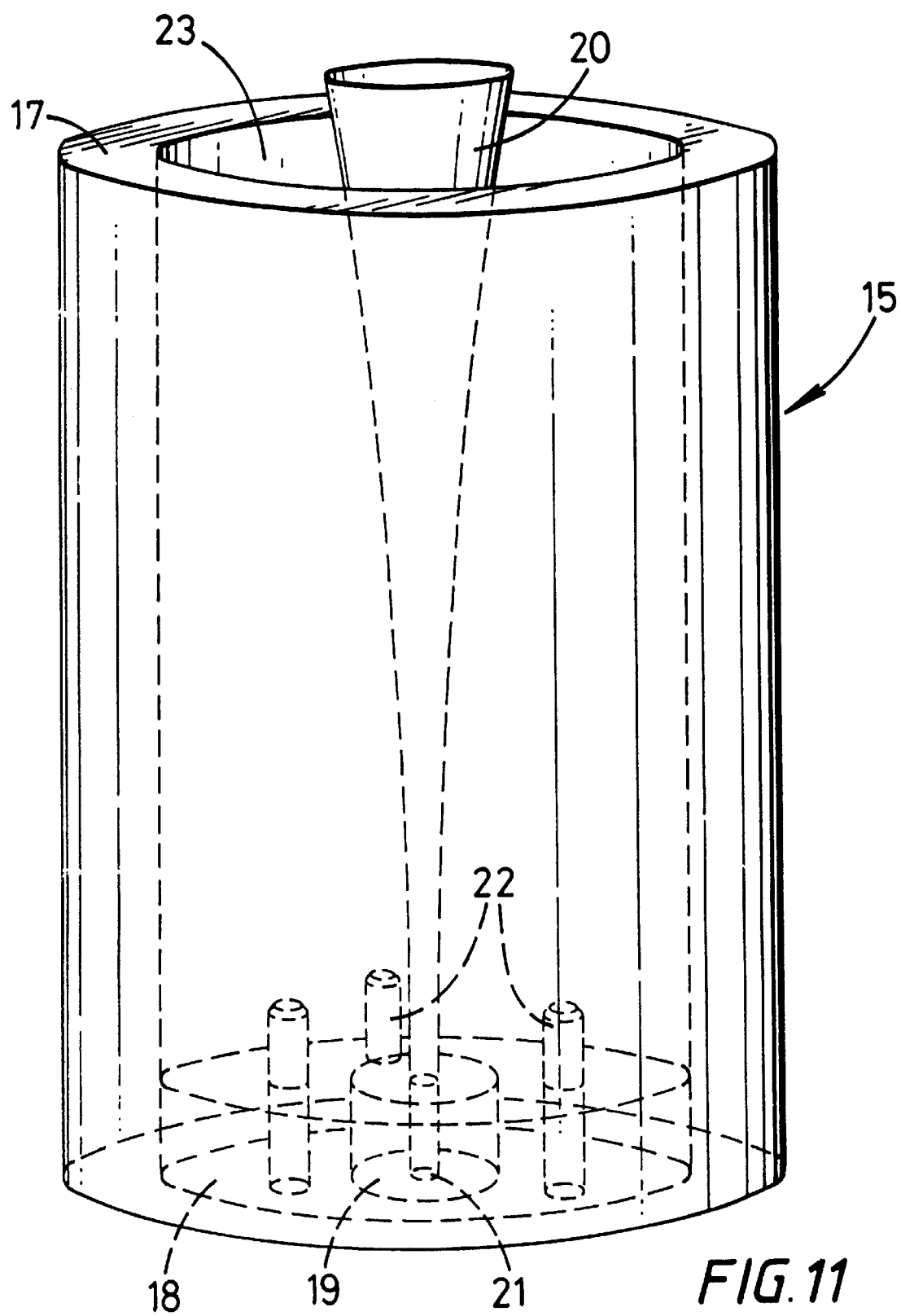
FIG. 11 is a perspective view showing a mould used to manufacture a funnel shaped die.

FIG. 11 shows the mould assembly 15 for forming the funnel shaped die 16.

The mould assembly 15 comprises a main cylinder or tube 17 which is open at the top, as viewed in FIG. 11, and closed at the bottom by an annular outer plug 18 and an inner plug 19, the outer plug 18 being a push fit within the tube or cylinder or tube 16.

There is a funnel shaped central core 20 made of tungsten carbide which is located coaxially with respect to the cylinder 16 with its wider end adjacent the top of the cylinder 16 and its narrow end fitting into a central court 21 in the inner plug 19.

The inner plug 19 is itself a sliding fit in the outer plug 18.

The outer plug 18 carries location pins 22 which together with the inner surface of the cylinder 16, the outer surface of the core member 20 and the top surfaces of the inner and outer plugs 18 and 19 are polished to facilitate removal of the die 16 after it has been formed in the mould 15.

The inner plug 19 has the accurately centrally positioned hole 21 which is later used to ensure that the folded transducer/multiplexer assembly FIG. 8 is positioned accurately concentrically with respect to the distal end of the body 2 of the catheter.

Figure 12:
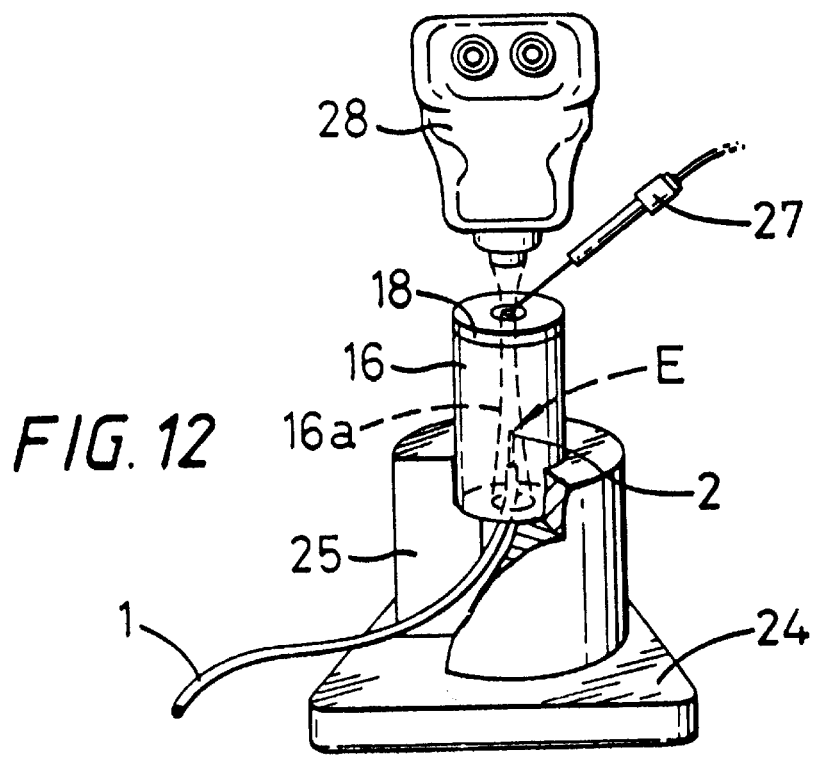
FIG. 12 is a perspective general arrangement view of apparatus for carrying out the method of the present invention.

The purpose of the locating pins 22 is to ensure that in subsequent reassembly of the die 16 and the plugs 18 and 19 in the apparatus shown in FIG. 12 the positional interrelationships of the die 16, outer plug 18 and inner plug 19 are accurately maintained.

The reason for having the inner plug 19 as well as the outer plug 18 is to enable access to be obtained by removal of the inner plug 19 in a subsequent moulding step in the manufacturing process.

Potting compound, e.g. a standard mould-making polyester resin is then injected into the annular space 23 between the cylinder 17 and the core 20 and allowed to set to form the die 16.

The funnel shaped core 20 is then withdrawn from the mould assembly and the moulded die 16 is withdrawn from a cylinder 17.

The assembly shown in FIG. 4 has a temporary pulling wire (not shown) connected to the end marked C, the other end of the wire then being inserted into the wide end of the funnel shaped passage 22 in the die and the wire is then drawn through the narrow end of the funnel shaped passage.

As the flat arrangement is drawn through the funnel shaped passage 16a it is caused to progressively wrap, fold or roll into a substantially cylindrical shape by the time it reaches the narrow end in the area marked D in FIG. 13.

The die 16 of the wrapped transducer/multiplexer assembly already located in the inner plug 19 is then positioned in the apparatus shown in FIG. 12.

This apparatus consists of a base 24 which carries a cylindrical support 25 (shown cut away for clarity) adapted to hold the moulded die 16 and the associated inner and outer plugs 18 and 19 respectively in the manner shown in more detail in the fragmentary exploded view of FIG. 13.

The distal end E of the body 2 of the catheter 1 is inserted into the funnel shaped passage 16a, as shown in FIG. 12, after the transducer array/multiplexer assembly has been converted from a flat to a cylindrical configuration, the cylindrical transducer array then being, at that time, located in the central hole 21 in the plug member 19.

A locating pin 26 is positioned accurately centrally with respect to the central hole 21 (as shown in FIG. 13) and then the catheter body 2 is pushed to bring its distal end into the position also shown in FIG. 14.

By means of the central hole 21 and the locating pin 26 it is possible to very accurately centre the cylindrical transducer array 3 with respect to the axis of the distal end of the catheter inner body 2.

The inner plug 19 is removed to make it easier to inject adhesive by means of an applicator 27 to secure the combined cylindrical transducer array 3 and square multiplexer 4 arrangement to the distal end of the catheter body 2.

In carrying out this operation the operator makes use of a microscope 28 to ensure accuracy.

Figure 15:
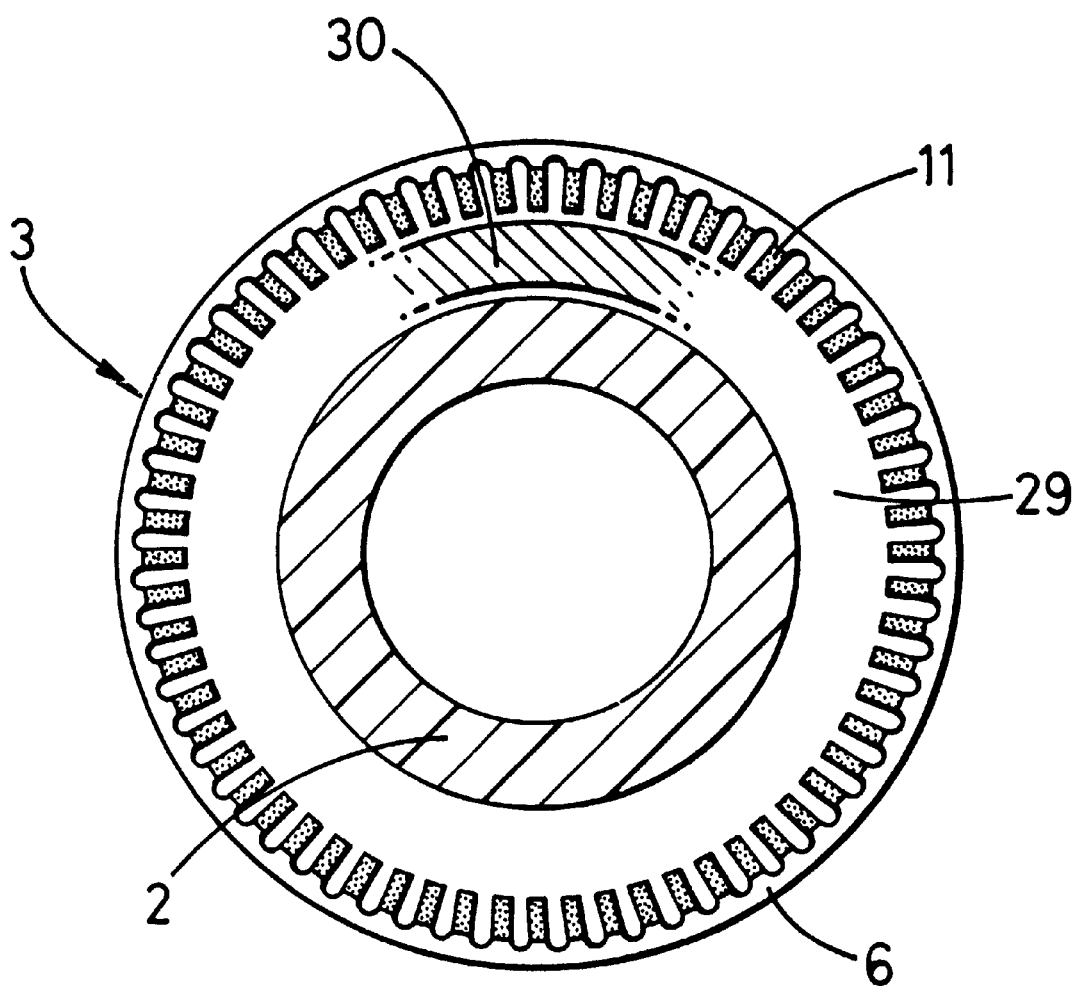
FIG. 15 is a view similar to FIG. 2 showing a preform which can be used in the method of assembling the transducer array on the distal end of the catheter.

The annular gap 29 between the distal end of the catheter inner body 2 and the annular transducer array 3 (see FIG. 15) is either filled entirely with the injected adhesive or part of the gap is filled by an adhesive preform 30 which has previously been attached to the distal end of the inner body 2 of the catheter. The adhesive used is an ultrasound backing layer material such as a suitable epoxy resin based compound. FIG. 15 illustrates the preform.

The material filling the annular space 29 thus serves two purposes, the first being to act as an adhesive and the second to act as an acoustic backing layer.

The wire interconnections or electrical leads are now bonded to the input/output pads. The preferable configuration for the interconnects is in the form of a sub-miniature flat ribbon cable which enables all the connections to be made in one operation with a suitable tool. By arranging the electrical configuration of the ribbon cable such that signal lines are alternated with ground lines, such a ribbon cable can provide low loss controlled-impedance and shielded interconnections.

An advantage of this design is that the injected adhesive does not have to define the relationship of the acoustic components, so rigidity is not a prime concern and the adhesive can have the optimum properties required for an acoustic backing layer. It could for example be a low viscosity epoxy resin.

In the preferred embodiment the first step is to print on a single piece of substrate material a number of circuits which represent the same number of finished transducer array/multiplexer assemblies. This permits efficient use of material, and simultaneous processing of a number of devices at once, saving time and cost.

There are a number of advantages provided by the method and construction of the present invention and in particular by the fact that in the finished assembly the flexible substrate is located radially outwardly with respect to the transducer array and the multiplexing elements.

One advantage, associated with the transducer array, is the fact that the flexible substrate protects the transducer array against foreign matter entering into the gaps between adjacent transducer elements. If the assembly were constructed with the flexible substrate radially inwardly with respect to the transducer array it would be necessary to provide a sealing layer around the outside of the transducer array in order to prevent the ingress of foreign matter into the gaps between adjacent transducer elements. This protective layer would have to be accurately formed in the cylindrical configuration and this would prove more difficult than forming a similar film or coating in the flat.

Another advantage of the present invention is that because the bases of the transducer elements lie on a circle having a greater diameter than would be the case were the flexible substrate to be radially inwardly with respect to the transducer array it is possible to construct a transducer array with a larger number of transducer elements, for a given overall outside diameter for the assembly, than would be the case were the flexible substrate to be located radially inwardly with respect to the transducer array. Alternatively, for a given number of transducer elements it would be possible, with the present invention, to construct an assembly having a smaller overall outside diameter than would be the case with the alternative construction discussed earlier.

A further advantage is that with the present invention any tendency for the planar assembly to unfold will press it tighter against the mould and thus make it more accurate in contrast with the case where the substrate is wrapped around a former (with the transducers on the outside) where any tendency to unwrap will give rise to inaccuracies in the final cylindrical shape.

Instead of using the method and apparatus described and shown in FIGS. 11 and 15 to convert the planar assembly into a cylindrical configuration other arrangements could be employed. For example a mould could be used into which the planar assembly is forced. This mould could comprise two semi-circular sectioned elements having means to draw the planar assembly into them by suction to make it conform to the internal shape of the mould.

FIG. 16

It may be that in manufacturing the assembly shown in FIGS. 4 to 10 the manufacturing process involved in producing the transducer array 3 is incompatible with the process used to manufacture the multiplexer arrangement 4.

Figure 16:
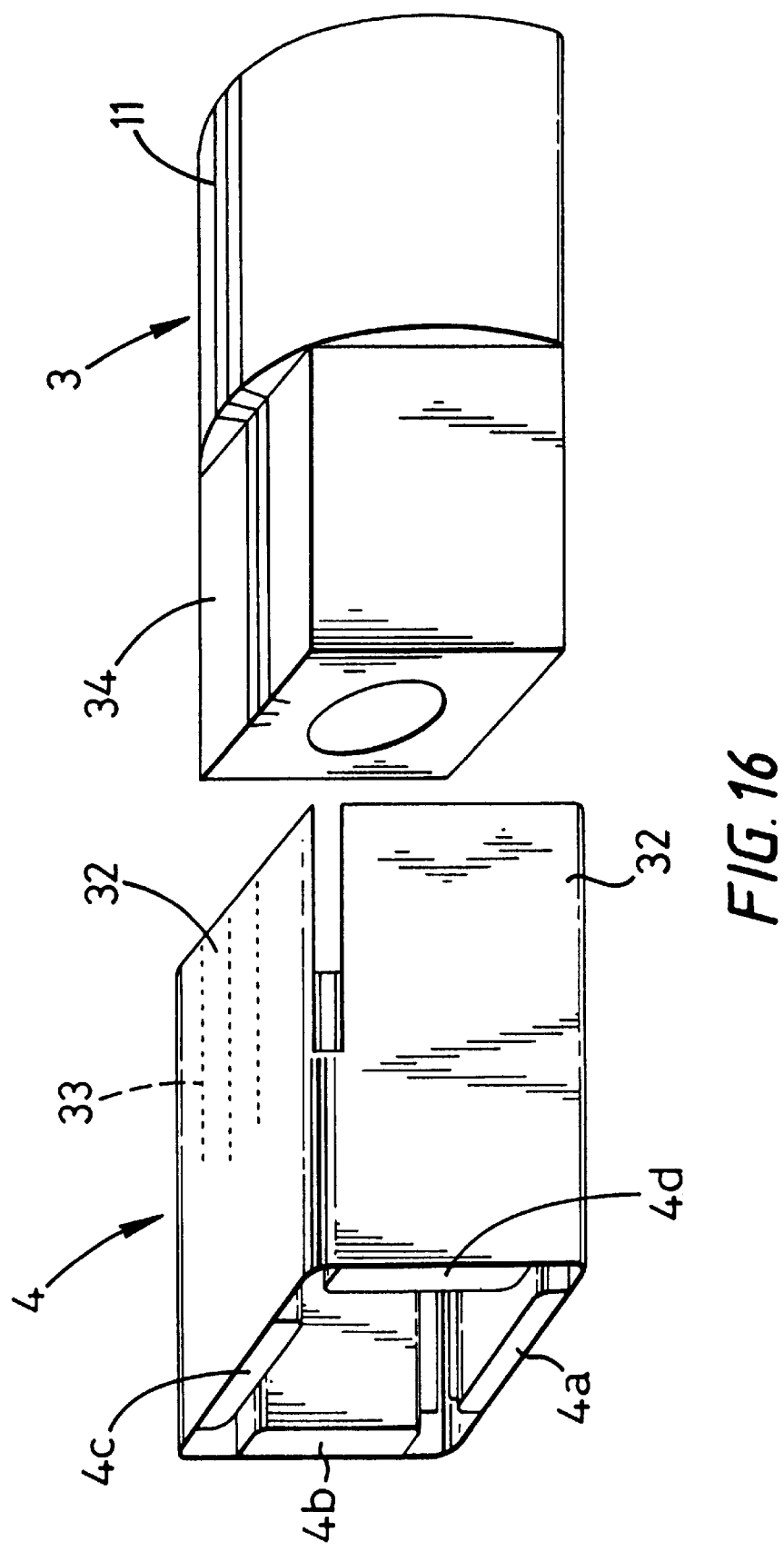
FIG. 16 is a perspective diagrammatic view of a further embodiment of the present invention.

Therefore in order to deal with this problem it is proposed to have the hybrid arrangement illustrated diagrammatically in FIG. 16.

In this arrangement the PZT transducer array 3 is formed as a separate three dimensional micro machined assembly similar to that disclosed in our earlier UK Patent Application No. 9116478 but with the bond pad area having a polygonal rather than a circular cross-section. In other words it is only the multiplexer arrangement 4 which is initially formed in-the-flat.

With this hybrid arrangement the bond pads for the array 3 are formed on the substrate carrying the multiplexer arrangement, the flexible substrate being provided with flaps 32 which carry the electrical tracks 33 so that the polygonal shaped multiplexer assembly 4 can then be slid over a correspondingly rectangular shaped spigot portion 34 of the transducer assembly 3.

We claim:

1. A catheter comprising:
   a distal end,
   a proximal end,
   a cylindrical array of ultrasound transducer elements,
   a flexible substrate,
   means for bonding the ultrasound transducer elements to the flexible substrate at the distal end of the catheter,
   a central tube forming part of the distal end of the catheter and having the cylindrical array around said central tube,
   the central tube having a bore for accommodating a guide wire therein,
   electrically conducting tracks carried on the flexible substrate, such tracks being in electrical contact with the transducer elements of the cylindrical array whereby the transducer elements can be energized through the conducting tracks, and
   at least three integrated circuits mounted on the distal end of the catheter, said integrated circuits being arranged in the form of a polygon around said distal end, each integrated circuit being carried by said flexible substrate.

2. A catheter as claimed in claim 1, wherein the flexible substrate is located radially outwardly of said integrated circuits, and the conducting tracks are carried on a radially inner surface of said flexible substrate.

3. A catheter as claimed in claim 1, wherein the integrated circuits and the cylindrical array are spaced from one another in a direction of a longitudinal axis of the catheter, both the integrated circuits and the cylindrical array being mounted on said flexible substrate, and at least one substantially longitudinal slot being formed at an intermediate portion in the flexible substrate between the integrated circuits and the cylindrical array in order to render said intermediate portion of the substrate relatively flexible.

4. A catheter as claimed in claim 1, wherein the integrated circuits and the cylindrical array are spaced from one another in a direction along the longitudinal axis of the catheter, both the integrated circuits and the cylindrical array being mounted on the flexible substrate, and an intermediate region of the substrate located between the integrated circuits and the cylindrical array being relatively flexible to permit the catheter to bend in this region.

5. A catheter as claimed in claim 4, wherein said intermediate region includes at least one substantially longitudinal slot formed between the integrated circuits and the cylindrical array in order to render said intermediate region of the substrate relatively flexible.

6. A catheter comprising:
   a distal end,
   a proximal end,
   a cylindrical array of ultrasound transducer elements,
   a flexible substrate,
   means for bonding the ultrasound transducer elements to the flexible substrate at the distal end of the catheter,
   a central tube forming part of the distal end of the catheter and having the cylindrical array around said central tube,
   the central tube having a bore for accommodating a guide wire therein,
   electrically conducting tracks carried on the flexible substrate, such tracks being in electrical contact with the transducer elements of the cylindrical array whereby the transducer elements can be energized through the conducting tracks, and
   the substrate comprises at least two laminae, the first lamina being flexible and acting as a second part of a two layer matching layer and having the conductive tracks thereon and the second lamina being sandwiched between said first lamina and said transducer elements which are carried thereon, the second lamina having a higher acoustic impedance than the first lamina and acting as a first part of the two layer matching layer.

* * * * *